(12) United States Patent
Xie et al.

(10) Patent No.: US 8,373,013 B2
(45) Date of Patent: Feb. 12, 2013

(54) PROCESS FOR COMBINING THE CATALYTIC CONVERSION OF ORGANIC OXYGENATES AND THE CATALYTIC CONVERSION OF HYDROCARBONS

(75) Inventors: Wenhua Xie, Beijing (CN); Genquan Zhu, Beijing (CN); Qiang Fu, Beijing (CN); Zhiguo Wu, Beijing (CN); Shaobing Yu, Beijing (CN); Yihua Yang, Beijing (CN); Qiang Liu, Beijing (CN); Zhiqiang Qiao, Beijing (CN); Xuhong Mu, Beijing (CN); Chaogang Xie, Beijing (CN); Yibin Luo, Beijing (CN); Jiushun Zhang, Beijing (CN); Xingtian Shu, Beijing (CN)

(73) Assignees: China Petroleum & Chemical Corporation, Beijing (CN); Research Institute of Petroleum Processing, SINOPEC, Beijing (CN)

( * ) Notice: Subject to any disclaimer, the term of this patent is extended or adjusted under 35 U.S.C. 154(b) by 267 days.

(21) Appl. No.: 12/373,586

(22) PCT Filed: Jul. 12, 2007

(86) PCT No.: PCT/CN2007/002134
§ 371 (c)(1),
(2), (4) Date: Feb. 11, 2009

(87) PCT Pub. No.: WO2008/009218
PCT Pub. Date: Jan. 24, 2008

(65) Prior Publication Data
US 2009/0318742 A1  Dec. 24, 2009

(30) Foreign Application Priority Data

Jul. 13, 2006  (CN) .......................... 2006 1 0091074

(51) Int. Cl.
*C01C 1/20* (2006.01)
(52) U.S. Cl. .............. 585/324; 208/49; 208/67; 208/78; 585/301; 585/304; 585/312; 585/313; 585/314; 585/638; 585/639; 585/640; 585/648; 585/653

(58) Field of Classification Search .................. 585/301, 585/304, 638, 639, 640, 648, 653, 13, 14, 585/240, 250, 312, 313, 314, 324; 208/108, 208/78, 113, 120.1, 155, 240, 49, 67
See application file for complete search history.

(56) References Cited

U.S. PATENT DOCUMENTS 3,702,886 A   11/1972  Argauer et al.
(Continued)

FOREIGN PATENT DOCUMENTS

| CN | 1504542 A | 6/2004 |
| EP | 130368 A1 * | 1/1985 |
| EP | 06118982.5 A1 * | 8/2006 |

OTHER PUBLICATIONS

Werther, "Fluidized Bed Reactors" in Ullmann's Encyclopedia of Industrial Chemistry, 2007, Wiley VCH, available on-line Apr. 15, 2007.*

(Continued)

*Primary Examiner* — In Suk Bullock
*Assistant Examiner* — Bradley Etherton
(74) *Attorney, Agent, or Firm* — Anova Law Group, PLLC; Allen (Zhi Yang) Xue

(57) ABSTRACT

A process for combining the catalytic conversion of organic oxygenates and the catalytic conversion of hydrocarbons: an organic oxygenate feedstock is contacted with a Y-zeolite containing catalyst to produce a reaction stream, and a coked catalyst and a product stream are obtained after separating the reaction stream; a hydrocarbon feedstock is contacted with a Y-zeolite containing catalyst to produce a reaction stream, a spent catalyst and a reaction oil vapor are obtained after separating the reaction stream, and the reaction oil vapor is further separated to give the products such as gas, gasoline and the like; a part or all of the coked catalyst and a part or all of the spent catalyst enter the regenerator for the coke-burning regeneration, and the regenerated catalyst is divided into two portions, wherein one portion returns to be contacted with the hydrocarbon feedstock, and the other portion, after cooling, returns to be contacted with the organic oxygenate feedstock. This process not only reasonably utilizes the excessive thermal energy of the hydrocarbon conversion, but also solves the problem of heat supply for the conversion of the organic oxygenate, thus ensuring the continuous catalytic conversion of the organic oxygenate.

35 Claims, 1 Drawing Sheet

U.S. PATENT DOCUMENTS

| | | | | |
|---|---|---|---|---|
| 3,969,426 A | * | 7/1976 | Owen et al. | 585/301 |
| 4,148,835 A | | 4/1979 | Chen et al. | |
| 4,467,133 A | * | 8/1984 | Chang et al. | 585/733 |
| 4,606,810 A | * | 8/1986 | Krambeck et al. | 208/74 |
| 4,781,815 A | * | 11/1988 | Pellet et al. | 208/120.15 |
| 4,881,592 A | * | 11/1989 | Cetinkaya | 165/104.16 |
| 4,935,568 A | * | 6/1990 | Harandi et al. | 585/300 |
| 5,191,142 A | * | 3/1993 | Marshall et al. | 585/640 |
| 5,232,675 A | | 8/1993 | Shu et al. | |
| 5,481,057 A | | 1/1996 | Bell et al. | |
| 5,582,711 A | * | 12/1996 | Ellis et al. | 208/76 |
| 5,914,433 A | | 6/1999 | Marker | |
| 6,049,017 A | | 4/2000 | Vora et al. | |
| 6,303,839 B1 | * | 10/2001 | Marker | 585/313 |
| 6,441,261 B1 | | 8/2002 | Kuechler et al. | |
| 6,441,262 B1 | * | 8/2002 | Fung et al. | 585/640 |
| 6,455,749 B1 | * | 9/2002 | Vaughn | 585/640 |
| 6,495,028 B1 | * | 12/2002 | Xu et al. | 208/69 |
| 7,029,571 B1 | * | 4/2006 | Bhattacharyya et al. | 208/76 |
| 2007/0007176 A1 | * | 1/2007 | Pinho et al. | 208/108 |

OTHER PUBLICATIONS

Communication from European Patent Office with a Supplementary European Search Report.

* cited by examiner

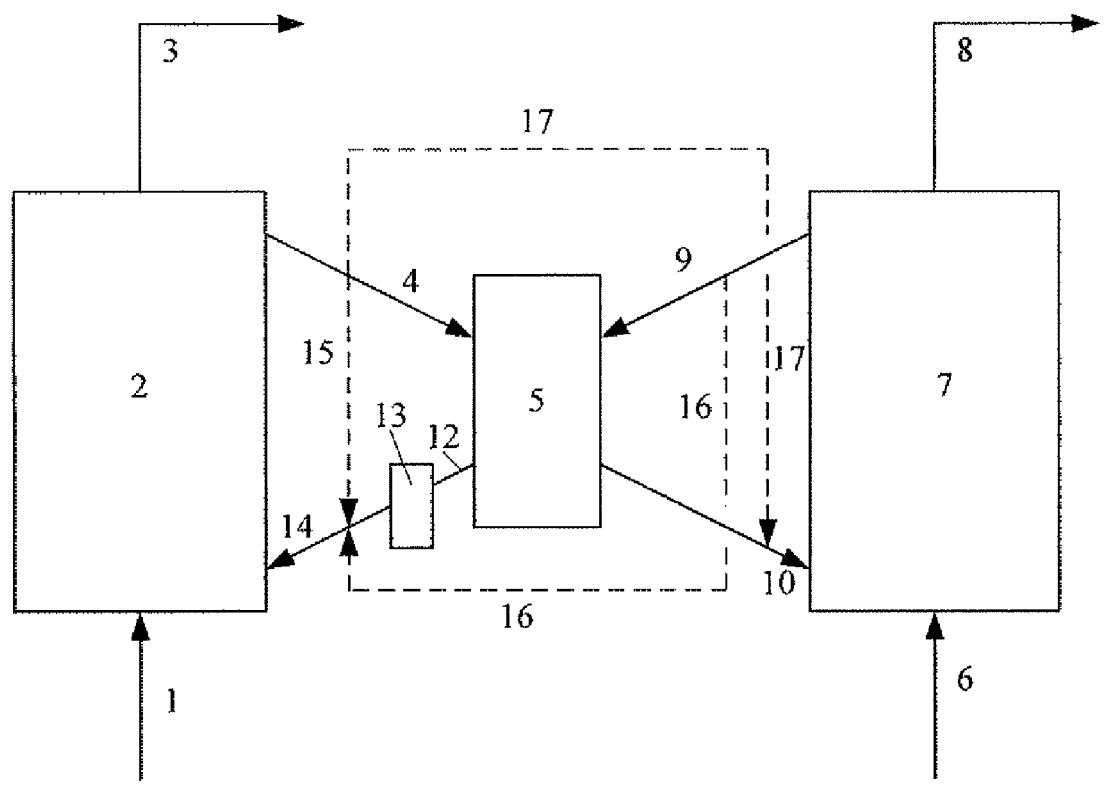

PROCESS FOR COMBINING THE CATALYTIC CONVERSION OF ORGANIC OXYGENATES AND THE CATALYTIC CONVERSION OF HYDROCARBONS

FIELD OF THE INVENTION

The present invention relates to a process for combining the catalytic conversion of organic oxygenates and the catalytic conversion of hydrocarbons.

BACKGROUND OF THE INVENTION

The global petroleum supply-demand contradiction is increasingly prominent at the beginning of the 21$^{st}$ century. Along with the increased demand for various petroleum and petrochemical products, the price of crude oil in the market is continuously increased. This situation leads to persisting high market-prices of important chemical products such as light olefins (especially ethylene and propylene) and light ethers (such as dimethyl ether, ethyl ether, etc), using petroleum and petrochemical products as feedstock. Therefore, it is one choice of solving these problems to seek for another substituting feedstock such as by-product ethanol from agriculture and forestry, and methanol prepared from natural gas or coal to produce light olefins and light ethers.

The process for preparing ethylene from ethanol is to carry out the dehydration reaction $CH_3CH_2OH \rightarrow CH_2=CH_2 + H_2O$ at 140-400° C. with a suitable catalyst. At the beginning of 1980's, India and Brazil built up industry-scale devices for converting ethanol to ethylene, using $SiO_2-Al_2O_3$ as catalyst and adopting fixed bed and fluidized bed reactors altogether. For the balance of heat, an additional fuel will be added when the catalyst is regenerated.

The process disclosed in U.S. Pat. No. 6,441,261 is to convert oxygenates (methanol, etc) to light olefins, e.g. ethylene and propylene, on a silicoaluminophosphate molecular sieve catalyst under a relative high pressure.

U.S. Pat. No. 6,303,839 and U.S. Pat. No. 5,914,433 convert oxygenates (methanol, etc) to light olefins and fractionate out the propylene and/or butene therein for cracking, thereby enhancing the yield of ethylene and propylene. Although the above processes also use fluidized bed operation, it is seen from the data of the examples that the yield of coke is only 2%. With a low yield of coke, the heat of the system is difficult to be balanced, and an external heat supply is generally needed.

U.S. Pat. No. 6,049,017 increases the yield of light olefins by separating the product containing $C_4$ components and converting them to ethylene and propylene on a non-molecular sieve catalyst. This process may be used in the catalytic cracking or the methanol dehydration for producing ethylene and propylene.

U.S. Pat. No. 4,148,835 uses a shape-selective molecular sieve catalyst and derivatives thereof to convert alcohols (especially methanol) to a product mainly containing light olefins, but this patent does not mention of the process.

The conventional process for preparing dimethyl ether (DME) from methanol is to carry out the methanol vapor phase dehydration with an acidic catalyst to give DME and other by-products such as $CO$, $CO_2$, $CH_4$, $C_2H_4$, $H_2$ and the like. Said acidic catalyst includes zeolite, active alumina, crystalline aluminosilicate, silica/alumina, cation exchange resins and the like.

The alcohol dehydration reaction is conducted at a certain temperature. Although coke deposition may occur during the reaction, the amount of the coke is insufficient to balance the heat of the process. In summary, all the prior arts provide the heat in a manner of supplying an external fuel, making the process too complicated or the energy consumption too high.

SUMMARY OF THE INVENTION

The object of the present invention is to provide a process for combining the catalytic conversion of organic oxygenates and the catalytic conversion of hydrocarbons.

According to the present invention, the process for combining the catalytic conversion of organic oxygenates and the catalytic conversion of hydrocarbons comprises the following steps:

(1) An organic oxygenate feedstock is contacted with a Y-zeolite containing catalyst to produce a reaction stream, and a coked catalyst and a product stream are obtained after separating the reaction stream;

(2) A hydrocarbon feedstock is contacted with a Y-zeolite containing catalyst to produce a reaction stream, a spent catalyst and a reaction oil vapor are obtained after separating the reaction stream, and the reaction oil vapor is further separated to give the products such as gas, gasoline and the like;

(3) A part or all of the coked catalyst in step (1) and a part or all of the spent catalyst in step (2) enter a regenerator for the coke-burning regeneration, and the regenerated catalyst is divided into two portions, wherein one portion returns to step (2), and the other portion returns to step (1) after cooling.

The content of the organic oxygenate in the organic oxygenate feedstock in the present invention is 10-100 wt %, preferably 50-100 wt %, and more preferably 90-100 wt %, and a small amount of impurities may be contained. The organic oxygenate is selected from the group consisting of alcohols, ethers, ketones, carboxylic acids, cyclic ethers, aldehydes, polyhydroxy compounds and mixtures thereof. The preferred organic oxygenate is selected from alcohols and ethers and mixtures thereof.

The carbon atom number of said alcohol is 1-10, preferably 1-5, and more preferably 1-2; and the hydroxyl group number of said alcohol is 1-3, and preferably 1. The alcohol is selected from the group consisting of alcohols having both the carbon atom number and the hydroxyl group number in the above range and mixtures thereof. Most preferably, said alcohol is methanol and/or ethanol. Said alcohol feedstock comes from the alcohols obtained by fermenting various agriculture crops and forest products and/or the alcohols obtained by gasification and synthesis from various fossil fuels such as natural gas, coal, tar sands, petroleum and the like.

The carbon atom number of said ethers is preferably 2-6, the carbon atom number of ketones is preferably 3-5, the carbon atom number of carboxylic acids is preferably 4-6, and the carbon atom number of aldehydes is preferably 1-5. The polyhydroxy compound mainly means carbohydrates, i.e. polyhydroxy aldehydes or polyhydroxy ketones, including monosaccharides (such as glucose), oligosaccharide (such as saccharose), polysaccharides (such as cellulose) and the like, and preferably it has a carbon number of 3-6.

Said hydrocarbon feedstock is selected from the group consisting of C4+ hydrocarbons, crude oil, gasoline, diesel oil, vacuum gas oil, coker gas oil, deasphalted oil, hydrogenated bottom, atmospheric residuum, vacuum residuum and mixtures thereof; and it is preferably selected from the group consisting of vacuum gas oil, coker gas oil, deasphalted oil, hydrogenated bottom, atmospheric residuum, vacuum residuum and mixtures thereof.

In one embodiment of the present invention, the organic oxygenate feedstock consists essentially of ethanol.

In one embodiment of the present invention, the organic oxygenate feedstock contains 1-100%, preferably 15-95%, more preferably 65-95% of ethanol by the weight of organic oxygenate feedstock. In the organic oxygenate feedstock, the remaining components is water and/or other organic oxygenate except from ethanol.

Said Y-zeolite containing catalyst may contain a Y-zeolite and an optional other molecular sieve, but not contain inorganic oxides and clay, wherein the weight ratio of the other molecular sieve to the Y-zeolite is 0-10. Said Y-zeolite containing catalyst preferably contains inorganic oxides and/or clay, a Y-zeolite, and an optional other molecular sieve, wherein the weight ratio of the other molecular sieve to the Y-zeolite is 0-10, and the total weight of the other molecular sieve and the Y-zeolite comprises 10-60% of the catalyst.

Said Y-zeolite includes Y-type zeolite and their derivative or modified zeolites, and is selected from the group consisting of Y, HY, REY, REHY, USY, REUSY and mixtures thereof.

Said other molecular sieve is one or more selected from meso porous zeolites, Beta-zeolites, and SAPO-molecular sieves.

Said meso porous zeolite includes ZRP series (rare earth-modified), ZSP series (iron-modified), ZSM series zeolites and their derivative or modified zeolites. For the more detailed description of ZRP, a reference may be made to U.S. Pat. No. 5,232,675. Said ZSM series zeolite is selected from the group consisting of ZSM-5, ZSM-11, ZSM-12, ZSM-22, ZSM-23, ZSM-35, ZSM38, ZSM-48, and other zeolites having a similar structure. For more detailed description of ZSM-5, a reference may be made to U.S. Pat. No. 3,702,886.

A more preferred Y-zeolite containing catalyst contains Y-zeolites, meso porous zeolites, inorganic oxides, and clay, wherein the weight ratio of the meso porous zeolite to the Y-zeolite is 0.1-10, and the total weight of the meso porous zeolite and the Y-zeolite accounts for 10-60% of total weight of the catalyst.

Said inorganic oxide is selected from the group consisting of alumina, silica, amorphous silica-alumina and mixtures thereof. The clay is kaolin and/or halloysite.

The reaction conditions in step (1) are a temperature of 50-500° C., a pressure (gauge) of 0-0.8 MPa, a weight ratio of the catalyst to the organic oxygenate feedstock of 0.001-50, and a weight hourly space velocity of 0.05-10 $h^{-1}$, preferably 0.1-8 $h^{-1}$.

The reaction conditions in step (2) are a temperature of 400-700° C., a pressure (gauge) of 0-0.8 MPa, a weight ratio of the catalyst to the hydrocarbon feedstock of 1-30, and a time of 1-10 seconds.

The catalytic conversion process in step (2) comprises conventional catalytic cracking processes and various family processes such as the DCC process, CPP process, MIP process, MIP-CGP process, MGD process, MGG process, ARGG process, SHMP process and the like.

The proportion of the coked catalyst in step (1) subjected to coke-burning is 0.001-100%, preferably 0.01-60%, more preferably 0.1-40% by the total weight of the coked catalyst. When a portion of the coked catalyst in step (1) enters the regenerator for the coke-burning regeneration, the remaining coked catalyst returns to step (1) and/or step (2), and said portion of the coked catalyst subjected to coke-burning comprises 0.001-99%, preferably 0.01-60%, more preferably 0.1-40% by the total weight of the coked catalyst.

The proportion of the spent catalyst in step (2) subjected to coke-burning is 1-100%, preferably 50-100%, more preferably 80-100% by the total weight of the spent catalyst. When a portion of the spent catalyst in step (2) enters the regenerator for the coke-burning regeneration, the remaining spent catalyst returns to step (1), and said portion of the spent catalyst comprises 1-99%, preferably 50-99%, more preferably 80-99% by the total weight of the spent catalyst.

The regeneration in step (3) is one-stage regeneration or two-stage regeneration, and said regenerated catalyst is a partially regenerated catalyst (i.e. half-regenerated catalyst) and/or a full regenerated catalyst. The weight ratio of the coked catalyst and the spent catalyst entering the regenerator for the coke-burning regeneration is no more than 1.0, preferably no more than 0.5, more preferably no more than 0.2.

The reactors used in step (1) and step (2) are both catalyst-movable reactors, and are selected from the group consisting of a fluidized bed, a riser, a descending transfer line reactor, a moving bed, a composite reactor of riser and fluidized bed, a composite reactor of riser and descending transfer line, a composite reactor of two or more risers, a composite reactor of two or more fluidized beds, a composite reactor of two or more descending transfer lines, and a composite reactor of two or more moving beds. Each of the above reactors may be divided into two or more reaction zones. The preferred reactor in step (1) is a fluidized bed, more preferably a dense-phase fluidized bed. The preferred reactor in step (2) is a riser. Said riser is one or more selected from an iso-diameter riser, an equal-velocity riser, and various variable-diameter risers. Said fluidized bed is one or more selected from a fixed fluidized bed, a particulate fluidization bed, a bubbling bed, a turbulent bed, a quick bed, a transfer bed, and a dense-phase fluidized bed.

An existing catalytic cracking reactor may be used as the aforesaid reactor. Alternatively, a necessary modification may be made to an existing catalytic cracking reactor. Also the reactors having a similar structure and function to an existing catalytic cracking reactor can be used.

The product separation device may be the same one shared in Step (1) and Step (2), or the product separation device used in Step (1) is different from that in Step (2). The excessive organic oxygenate separated in step (1) may return to step (1). The $C_4^+$ light hydrocarbons separated in step (2) may return to step (1) and/or step (2).

The regenerated catalyst returning to the reactor of step (1) is first cooled down to 50-650° C. in a direct heat exchange mode or an indirect heat exchange mode. The direct heat exchange mode is to carry out heat exchange by directly contacting the regenerated catalyst with the air having a relatively low temperature. The air is a part or all of the air compressed by an air compressor and delivered to the regenerator, that is, the high temperature thermal energy from a portion of regenerated catalyst is used to preheat the air entering the regeneraton. The direct heat exchanger is in a type of fluidized bed or riser, and the cooled catalyst separated by a cyclone separator enters the catalytic conversion reactor of the organic oxygenate after stripping off the gas impurities (nitrogen, oxygen, carbon dioxide and the like) with the hot steam. The indirect heat exchange mode is to use an indirect heat exchanger, wherein the hot catalyst passes through the tube side and the steam passes through the shell side.

The process for combined catalytic conversion of organic oxygenates and hydrocarbons according to the present invention, not only reasonably utilizes the excessive thermal energy of the hydrocarbon conversion, but also solves the problem of heat supply for the conversion of the organic oxygenate, thus ensuring the continuous catalytic conversion of the organic oxygenate.

BRIEF DESCRIPTION OF THE DRAWINGS

FIG. 1 is a schematic flowsheet of the process for combined catalytic conversion of organic oxygenates and hydrocarbons according to an embodiment of the present invention.

PREFERRED EMBODIMENTS OF THE INVENTION

The process of the present invention will be further illustrated in reference to the drawing, but the present invention is not limit thereto.

FIG. 1 is a schematic flowsheet of the process for combined catalytic conversion of organic oxygenates and hydrocarbons according to an embodiment of the present invention.

An organic oxygenate feedstock from line 1 is introduced into the reactor 2 and contacted with a Y-zeolite containing regenerated catalyst from line 14 to react at 50-500° C., under a pressure (gauge) of 0-0.8 MPa, at a weight ratio of the catalyst to the organic oxygenate feedstock of 0.001-50, with a weight hourly space velocity of 0.1-10 $h^{-1}$. A coked catalyst and a product stream are obtained after separating the reaction stream, which is withdrawn through the line 3 and further separated to give the products, and the excessive organic oxygenate feedstock is recycled for use (not shown in the figure). The coked catalyst may be partially or completely introduced into the regenerator 5 through the line 4 for the coke-burning regeneration, and a portion of the coked catalyst may return to the reactor 2 sequentially through the lines 15 and 14 or return to the reactor 7 sequentially through the lines 17 and 10.

The hydrocarbon feedstock from line 6 is introduced into the reactor 7 and contacted with a Y-zeolite containing regenerated catalyst from the line 10 to react at 400-700° C., under a pressure (gauge) of 0-0.8 MPa, at a weight ratio of the catalyst to the hydrocarbon feedstock of 1-30, with a time of 1-10 s. A spent catalyst and a reaction oil vapor are obtained after separating the reaction stream, wherein the reaction oil vapor is withdrawn through the line 8 and further separated to give the products such as gas, gasoline, diesel oil and the like(not shown in the figure). After stripping, the spent catalyst is completely or partially introduced into the regenerator 5 through the line 9 for the coke-burning regeneration, and a portion of the spent catalyst may return to the reactor 2 sequentially through the lines 16 and 14.

The weight ratio of the coked catalyst and the spent catalyst entering the regenerator for the coke-burning regeneration is no more than 1.0, preferably no more than 0.5, more preferably no more than 0.2. The regenerated catalyst, which is coke-burning regenerated in the regenerator 5, is divided into two portions, wherein one portion returns to the reactor 7 through line 10, and the other portion sequentially enters the heat exchanger 13 through the line 12, cools therein, and then returns to the reactor 2 through the line 14.

The process of the present invention will further be illustrated by the following examples, but the present invention is not limit thereto.

EXAMPLE 1

The organic oxygenate feedstock and hydrocarbon feedstock used in this example were an ethanol feedstock containing 95% ethanol brewed from grains and vacuum gas oil (VGO), respectively, and the properties of VGO are shown in Table 1. The catalyst used in this example was CGP-1 (containing 25 wt % of REY-zeolite, 10 wt % of ZSP-zeolite, and the balanced support, all based on the total weight of the catalyst) produced by SINOPEC Catalyst Company Qilu Division.

The ethanol feedstock was introduced into a fluidized bed reactor and contacted with the CGP-1 catalyst to react at 340° C., under a pressure (gauge) of 0.1 MPa, at a weight ratio of the catalyst to the ethanol feedstock (catalyst/alcohol ratio) of 1, with a weight hourly space velocity of 1.0 $h^{-1}$. A coked catalyst and a product stream were obtained after separating the reaction stream, wherein the product stream was further separated to give the target product of ethylene. The product distribution is shown in Table 2. The coked catalyst was divided into two portions, wherein 20 wt % of the coked catalyst was introduced into the regenerator for the coke-burning regeneration, and the remaining 80 wt % of the coked catalyst retuned to the fluidized bed reactor through the inner recycle.

The preheated VGO was injected into a riser reactor after the steam atomization at a weight ratio of the steam to VGO was 0.1:1. VGO was contacted with hot CGP-1 catalyst in the riser to react at 500° C., under a pressure (gauge) of 0.1 MPa, at a weight ratio of the catalyst to VGO (catalyst/oil ratio) of 6, with a reaction time of 3 seconds. The mixture of the reaction oil vapor and the catalyst rose along the riser to the outlet of the riser, and then the reaction product stream and the spent catalyst were separated. The reaction product stream was introduced into the settler and then into the subsequent separation system to further separate into various products. The product distribution is shown in Table 2. The spent catalyst entered the stripper under the action of gravity to strip with the steam, and it was then introduced into the regenerator for the coke-burning regeneration.

20 wt % of the coked catalyst and all the spent catalyst were regenerated in the regenerator, wherein the weight ratio of the coked catalyst and the spent catalyst entering the regenerator for the coke-burning regeneration is about 0.02. After the regeneration, the regenerated catalyst were divided into two portions, wherein 85 wt % of the regenerated catalyst, having a temperature of 680° C., retuned to the riser for the recycling use, and the remaining 15 wt % of the regenerated catalyst was cooled down to 410° C. and retuned to the fluidized bed for the recycling use.

The testing results demonstrated that by combining the catalytic conversion of ethanol and the catalytic conversion of hydrocarbons, the heat between the two conversions can be balanced, and there is no need for the external fuel or other heat sources.

EXAMPLE 2

The organic oxygenate feedstock and hydrocarbon feedstock used in this example were methanol (chemically pure, produced by Xinle Chemicals plant, Hebei Province) and the blend of vacuum gas oil (VGO) with 30 wt % of atmospheric residuum, respectively. The properties of the atmospheric residuum are shown in Table 1. The catalyst used in this example was CGP-2 (containing 30 wt % of USY-zeolite, 5 wt % of ZSP-zeolite, and the balanced support, all based on the total weight of the catalyst) produced by SINOPEC Catalyst Company Qilu Division.

A liquid methanol feedstock was introduced into a fluidized bed reactor and contacted with the CGP-2 catalyst to react at 250° C., under a pressure (gauge) of 0.1 MPa, at a weight ratio of the catalyst to the methanol feedstock (catalyst/alcohol ratio) of 6, with a weight hourly space velocity of 3 $h^{-1}$. A coked catalyst and a product stream were obtained after separating the reaction stream, wherein the product stream was further separated to give the target product of dimethyl ether. The product distribution is shown in Table 3. The excessive methanol returned to the fluidized bed reactor. The coked catalyst was divided into two portions, wherein 50 wt % of the coked catalyst was introduced into the regenerator for the coke-burning regeneration, and the remaining 50 wt % of the coked catalyst retuned to the fluidized bed reactor through the inner recycle.

The preheated mixed feedstock oil of VGO and atmospheric residuum was injected into a riser reactor after the steam atomization at a weight ratio of steam to the mixed feed stock oil of 0.05:1. The mixed feedstock oil was contacted with a hot regenerated catalyst in the riser to react at 500° C., under a pressure (gauge) of 0.1 MPa, at a weight ratio of the catalyst to the mixed feedstock oil (catalyst/oil ratio) of 6, with a reaction time of 3 seconds. The mixture of the reaction oil vapor and the catalyst rose along the riser to the outlet of the riser, and then the reaction product stream and the spent catalyst were separated. The reaction product stream was introduced into the settler and then into the subsequent separation system to further separate into various products. The product distribution is shown in Table 3. The spent catalyst entered the stripper under the action of gravity to strip with the steam, and it was then introduced into the regenerator for the coke-burning regeneration.

50 wt % of the coked catalyst and all the spent catalyst were regenerated in the regenerator, wherein the weight ratio of the coked catalyst and the spent catalyst entering the regenerator for the coke-burning regeneration is about 0.1. After the regeneration, the regenerated catalyst were divided into two portions, wherein 90 wt % of the regenerated catalyst having a temperature of 690° C., retuned to the riser for the recycling use, and the remaining 10 wt % of the regenerated catalyst cooled down to 540° C. and retuned to the fluidized bed for the recycling use.

The testing results demonstrated that by combining the catalytic conversion of methanol and the catalytic conversion of hydrocarbons, the heat between the two conversions can be balanced, and there is no need for the external fuel or other heat sources.

EXAMPLE 3

The process was identical to Example 1, except that the feedstock was ethyl ether instead of ethanol. The reaction results are shown in Table 4, wherein the weight ratio of the coked catalyst and the spent catalyst entering the regenerator for the coke-burning regeneration is about 0.01.

EXAMPLES 4-6

The processes were identical to Example 1, except that the feedstocks were respectively propanol, butanol and glycerine instead of ethanol. The reaction results of the alcohols are shown in Table 5, wherein the weight ratios of the coked catalyst and the spent catalyst entering the regenerator for the coke-burning regeneration are about 0.03, 0.005, 0.001, respectively.

EXAMPLE 7

The organic oxygenate feedstock and hydrocarbon feedstock used in this example were methanol (chemically pure, produced by Xinle Chemicals plant, Hebei Province) and the blend of vacuum gas oil (VGO) with 30 wt % of atmospheric residuum, respectively, and the properties of the atmospheric residuum are shown in Table 1. The catalyst used in this example was MPO51 (containing 5 wt % of USY-zeolite, 30 wt % of ZSP-zeolite, and the balanced support, all based on the total weight of the catalyst) produced by SINOPEC Catalyst Company Qilu Division.

A methanol feedstock was introduced into a fluidized bed reactor and contacted with the MPO51 catalyst to react at 550° C., under a pressure (gauge) of 0.1 MPa, at a weight ratio of the catalyst to methanol feedstock (catalyst/alcohol ratio) of 2, with a weight hourly space velocity of 1.2 h$^{-1}$. A coked catalyst and a product stream were obtained after separating the reaction stream, wherein the product stream was further separated to give the target product of propylene. The product distribution is shown in Table 6. The excessive methanol retuned to the fluidized bed reactor. The coked catalyst was divided into two portions, wherein 50 wt % of the coked catalyst was introduced into the regenerator for the coke-burning regeneration, and the remaining 50 wt % of the coked catalyst retuned to the fluidized bed reactor through the inner recycle.

The preheated mixed feedstock oil of VGO and atmospheric residuum was injected into the riser reactor after the steam atomization at a weight ratio of steam to the mixed feedstock oil of 0.05:1. The mixed feedstock oil was contacted with the hot regenerated catalyst in the riser to react at 500° C., under a pressure (gauge) of 0.1 MPa, at a weight ratio of the catalyst to the mixed feedstock oil (catalyst/oil ratio) of 6, with a reaction time of 3 seconds. The mixture of the reaction oil vapor and the catalyst rose along the riser to the outlet of the riser, and then the reaction product stream and the spent catalyst were separated. The reaction product stream was introduced into the settler and then into the subsequent separation system to further separate into various products. The product distribution is shown in Table 6. The spent catalyst entered the stripper under the action of gravity to strip with the steam, and it was then introduced into the regenerator for the coke-burning regeneration.

50 wt % of the coked catalyst and all the spent catalyst regenerated in the regenerator, wherein the weight ratio of the coked catalyst and the spent catalyst entering the regenerator for the coke-burning regeneration is about 0.03. After the regeneration, the regenerated catalyst were divided into two portions, wherein 90 wt % of the regenerated catalyst, having a temperature of 690° C., retuned to the riser for the recycling use, and the remaining 10 wt % of the regenerated catalyst was cooled down to 600° C. and retuned to the fluidized bed for the recycling use.

The testing results demonstrated that by combining the catalytic conversion of methanol and the catalytic conversion of hydrocarbons, the heat between the two conversions can be balanced, and there is no need for the external fuel or other heat sources.

EXAMPLES 8-9

The processes were identical to Example 3, except that the feedstocks were ethanol aqueous solutions, containing 15% and 50% of ethanol, respectively, instead of ethanol (95%). The target product was ethyl ether. The reaction results are shown in Table 7, wherein the weight ratios of the coked catalyst and the spent catalyst entering the regenerator for the coke-burning regeneration are about 0.02, 0.015, respectively.

TABLE 1

| Feedstock Properties | VGO | Atmospheric residuum |
| --- | --- | --- |
| Density (20° C.), g/cm$^3$ | 0.9071 | 0.9387 |
| Sulfur content, ppm | 7800 | 12000 |
| Nitrogen content, ppm | 600 | 647 |
| Carbon residue, m % | 0.1 | 9.2 |
| C, m % | 86.43 | 87.05 |
| H, m % | 12.48 | 11.83 |
| Kinematic viscosity, mm$^2$/s | | |
| 80° C. | 21.28 | 325.1 |
| 100° C. | 11.32 | 129.5 |
| Freezing point, ° C. | 35 | 45 |
| True boiling point, ° C. | >350 | >450 |
| Vanadium, ppm | 0.3 | 1.7 |
| Nickel, ppm | 4.2 | 30 |

TABLE 2

| Example 1 | Ethanol feedstock |
| --- | --- |
| Catalytic conversion of organic oxygenate | |
| Reaction conditions | |
| Temperature, ° C. | 340 |
| Pressure (gauge), MPa | 0.1 |
| Catalyst/alcohol ratio | 1 |
| WHSV, h$^{-1}$ | 1.0 |
| Product distribution, vol % | |
| Ethylene | 95.79 |
| Propylene | 1.18 |
| Total C$_4$ hydrocarbons | 0.72 |
| Total C$_5$ hydrocarbons | 0.70 |
| C$_6^+$ hydrocarbons | 0.54 |
| Conversion of ethanol, % | 99.1 |
| Selectivity to ethylene, % | 95.2 |
| Carbon base ethylene yield*, m % | 89.52 |
| Catalytic conversion of hydrocarbons | |
| Reaction conditions | |
| Temperature, ° C. | 500 |
| Pressure (gauge), MPa | 0.1 |
| Catalyst/oil ratio | 6 |
| Time, s | 3 |
| Product distribution, wt % | |
| Dry gas | 10.56 |
| LPG | 44.78 |
| Gasoline | 21.32 |
| Diesel oil | 4.89 |
| Heavy oil | 3.18 |
| Coke | 15.28 |

*Carbon base ethylene yield = Carbon content in the target product/carbon content in the organic oxygenate feedstock

TABLE 3

| Example 2 | Methanol feedstock |
| --- | --- |
| Catalytic conversion of organic oxygenate | |
| Reaction conditions | |
| Temperature, ° C. | 250 |
| Pressure (gauge), MPa | 0.1 |
| Catalyst/alcohol ratio | 6 |
| WHSV, h$^{-1}$ | 3.0 |
| Product distribution, vol % | |
| DME | 53.11 |
| Light hydrocarbons | 0.90 |
| Water | 25.41 |
| Coke | 1.12 |

TABLE 3-continued

| Example 2 | Methanol feedstock |
| --- | --- |
| Unconverted methanol | 19.46 |
| Conversion of methanol, % | 80.54 |
| Selectivity to DME, % | >98 |
| Catalytic conversion of hydrocarbons | |
| Reaction conditions | |
| Temperature, ° C. | 500 |
| Pressure (gauge), MPa | 0.1 |
| Catalyst/oil ratio | 6 |
| Time, s | 3 |
| Product distribution, wt % | |
| Dry gas | 3.17 |
| LPG | 18.04 |
| Gasoline | 48.26 |
| Diesel oil | 18.73 |
| Heavy oil | 4.56 |
| Coke | 7.24 |

TABLE 4

| Example 3 | Ethyl ether feedstock |
| --- | --- |
| Catalytic conversion of organic oxygenate | |
| Reaction conditions | |
| Temperature, ° C. | 360 |
| Pressure (gauge), MPa | 0.1 |
| Catalyst/ether ratio | 10 |
| WHSV, h$^{-1}$ | 1.0 |
| Product distribution, vol % | |
| Ethylene | 83.57 |
| C$_3^+$ | 13.52 |
| Coke | 2.72 |
| Liquid | 0.19 |
| Catalytic conversion of hydrocarbons | |
| Reaction conditions | |
| Temperature, ° C. | 550 |
| Pressure (gauge), MPa | 0.1 |
| Catalyst/oil ratio | 6 |
| Time, s | 3 |
| Product distribution, wt % | |
| Dry gas | 10.56 |
| LPG | 44.78 |
| Gasoline | 21.32 |
| Diesel oil | 4.89 |
| Heavy oil | 3.18 |
| Coke | 15.28 |

TABLE 5

| Example | 4 | 5 | 6 |
| --- | --- | --- | --- |
| Feedstock | Propanol | Butanol | Glycerine |
| Catalytic conversion of organic oxygenates | | | |
| Reaction conditions | | | |
| Temperature, ° C. | 150 | 480 | 60 |
| Pressure (gauge), MPa | 0.1 | 0.1 | 0.1 |
| Catalyst/alcohol ratio | 25 | 45 | 0.005 |
| WHSV, h$^{-1}$ | 5 | 10 | 0.1 |
| Conversion of feedstock, % | 90 | 87 | 96 |
| Selectivity to target products, % | Propylene/92 | C4 olefins/95 | Acrolein/71 |

TABLE 6

| Example 7 | Methanol feedstock |
|---|---|
| Catalytic conversion of organic oxygenate | |
| Reaction conditions | |
| Temperature, °C. | 550 |
| Pressure (gauge), MPa | 0.1 |
| Catalyst/alcohol ratio | 2 |
| WHSV, $h^{-1}$ | 1.2 |
| Product distribution, vol % | |
| Ethylene* | 6.62 |
| Propylene* | 42.79 |
| Other light hydrocarbons* | 39.44 |
| Water | 57.36 |
| Coke | 1.12 |
| Unconverted methanol | 0.46 |
| Conversion of methanol, % | 99.89 |
| Selectivity to propylene*, % | >30 |
| Catalytic conversion of hydrocarbons | |
| Reaction conditions | |
| Temperature, °C. | 500 |
| Pressure (gauge), MPa | 0.1 |
| Catalyst/oil ratio | 6 |
| Time, s | 3 |
| Product distribution, wt % | |
| Dry gas | 3.17 |
| LPG | 18.04 |
| Gasoline | 48.26 |
| Diesel oil | 18.73 |
| Heavy oil | 4.56 |
| Coke | 7.24 |

*Based on the total amount of hydrocarbon products excluding water

TABLE 7

| Example | 8 | 9 |
|---|---|---|
| Feedstock | 15% ethanol | 50% ethanol |
| Catalytic conversion of organic oxygenate | | |
| Reaction conditions | | |
| Temperature, °C. | 150 | 200 |
| Pressure (gauge), MPa | 0.1 | 0.1 |
| Catalyst/alcohol ratio | 20 | 5 |
| WHSV, $h^{-1}$ | 6 | 9 |
| Conversion of feedstock | 70 | 88 |
| Product distribution, vol % | | |
| Ethylene | 9.0 | 15.3 |
| Ethyl ether | 89.88 | 83.51 |
| Propylene | 0.18 | 0.23 |
| Total $C_4$ hydrocarbons | 0.53 | 0.35 |
| Total $C_5$ hydrocarbons | 0.09 | 0.20 |
| $C_6^+$ hydrocarbons | 0.32 | 0.41 |

The invention claimed is:

1. A process for combining the catalytic conversion of organic oxygenates and the catalytic conversion of hydrocarbons, comprising the following steps:
   (1) reacting an organic oxygenate feedstock in the presence of a first portion of a regenerated Y-zeolite containing catalyst to produce a first product stream in a first reactor, wherein said first portion of the regenerated Y-zeolite containing catalyst becomes a coked catalyst, wherein said first product stream is separated in a first separation unit to obtain olefins;
   (2) reacting a petroleum-based hydrocarbon feedstock in the presence of a second portion of the regenerated Y-zeolite containing catalyst to produce a a second product stream in a second reactor, wherein the second portion of the regenerated Y-zeolite containing catalyst becomes a spent catalyst, wherein the second product stream is separated in a second separation unit to obtain products comprising LPG, gasoline, and diesel oil;
   (3) regenerating a mixture of the coked catalyst and the spent catalyst in a regenerator by coke-burning to obtain the regenerated Y-zeolite containing catalyst, wherein the mixture comprises all or a part of the coked catalyst and all or a part of the spent catalyst;
   (4) obtaining from the regenerated Y-zeolite containing catalyst the first portion of the regenerated Y-zeolite containing catalyst and the second portion of the regenerated Y-zeolite containing catalyst;
   (5) cooling the first portion of the regenerated Y-zeolite containing catalyst;
   (6) feeding the first portion of the regenerated Y-zeolite containing catalyst into the first reactor after the cooling step so that the first portion of the regenerated Y-zeolite containing catalyst supplies heat that substantially matches heat required for the conversion of the organic feedstock in the first reactor, wherein the conversion of the organic feedstock in the first reactor is endothermic; and
   (7) feeding the second portion of the regenerated Y-zeolite containing catalyst into the second reactor.

2. The process according to claim 1, characterized in that the content of the organic oxygenate in said organic oxygenate feedstock is 10-100% by weight.

3. The process according to claim 1 or 2, characterized in that said organic oxygenate is selected from the group consisting of alcohols, ethers, ketones, carboxylic acids, cyclic ethers, aldehydes, polyhydroxy compounds, and mixtures thereof.

4. The process according to claim 1 or 2, characterized in that said organic oxygenate is selected from the group consisting of alcohols, esters, and mixtures thereof.

5. The process according to claim 3, characterized in that the carbon atom number of said alcohols ranges from 1 to 10, and the hydroxyl group number of said alcohols ranges from 1 to 3.

6. The process according to claim 3, characterized in that the carbon atom number of said alcohols ranges from 1 to 5, and the hydroxyl group number is 1.

7. The process according to claim 3, characterized in that the carbon atom number of said ethers ranges from 2 to 6.

8. The process according to claim 3, characterized in that the carbon atom number of said ketones ranges from 3 to 5, the carbon atom number of said carboxylic acids ranges from 2 to 4, the carbon atom number of cyclic ethers ranges from 4 to 6, and the carbon atom number of aldehydes ranges from 1 to 5.

9. The process according to claim 3, characterized in that said polyhydroxy compound is polyhydroxy aldehydes or polyhydroxy ketones, and their carbon number ranges from 3 to 6.

10. The process according to claim 1, characterized in that said petroleum-based hydrocarbon feedstock is selected from the group consisting of C4+ hydrocarbons, crude oil, gasoline, diesel oil, vacuum gas oil, coker gas oil, deasphalted oil, hydrogenated bottom, atmospheric residuum, vacuum residuum, and mixtures thereof.

11. The process according to claim 1, characterized in that said petroleum-based hydrocarbon feedstock is selected from the group consisting of vacuum gas oil, coker gas oil, deasphalted oil, hydrogenated bottom, atmospheric residuum, vacuum residuum, and mixtures thereof.

12. The process according to claim 1, characterized in that said regenerated Y-zeolite containing catalyst comprises a Y-zeolite and one or more other molecular sieves.

13. The process according to claim 12, characterized in that said Y-zeolite containing catalyst further comprises inorganic oxides and/or clay.

14. The process according to claim 12 or 13, characterized in that said other molecular sieve is one or more selected from meso porous zeolites, Beta-zeolites, and SAPO-molecular sieves.

15. The process according to claim 12 or 13, characterized in that the weight ratio of said other molecular sieve to the Y-zeolite is less than or equal to 10.

16. The process according to claim 1, characterized in that said Y-zeolite containing catalyst comprises Y-zeolites, meso porous zeolites, inorganic oxides, and clay.

17. The process according to claim 1, 12 or 13, characterized in that said Y-zeolite is selected from the group consisting of Y, HY, REY, REHY, USY, REUSY, and mixtures thereof.

18. The process according to claim 16, characterized in that said meso porous zeolite is chosen from ZRP series zeolites, ZSP series zeolites, ZSM series zeolites, or mixtures thereof.

19. The process according to claim 16, characterized in that the weight ratio of said meso porous zeolite to the Y-zeolite ranges from 0.1 to 10, and the total weight of the meso porous zeolite and the Y-zeolite accounts for 10-60% of total weight of the regenerated Y-zeolite containing catalyst.

20. The process according to claim 13, characterized in that said inorganic oxide is selected from the group consisting of alumina, silica, amorphous silica-alumina, and mixtures thereof, and the clay is kaolin clay and/or halloysite.

21. The process according to claim 1, characterized in that step (1) is carried out at a temperature of 50-500° C., a gauge pressure of 00.8 MPa, a weight ratio of the first portion of the regenerated Y-zeolite containing catalyst to the organic oxygenate feedstock of 0.001-50, and a weight hourly space velocity of 0.05-10 h$^{-1}$.

22. The process according to claim 1, characterized in that step (2) is carried out at a temperature of 400-700° C., a gauge pressure of 00.8 MPa, a weight ratio of the second portion of the regenerated Y-zeolite containing catalyst to the hydrocarbon feedstock of 1-30, and a reaction time of 1-10 seconds.

23. The process according to claim 1, characterized in that the mixture of the coked catalyst and the spent catalyst regenerated in the regenerator comprises 0.0001-100% by weight of the total amount of the coked catalyst.

24. The process according to claim 1 or 23, characterized in that 0.001-99% by weight of the total amount of the coked catalyst is not in the mixture of the coked catalyst and the spent catalyst regenerated in the regenerator.

25. The process according to claim 1, characterized in that the mixture of the coked catalyst and the spent catalyst regenerated in the regenerator comprises 1-100% by weight of the total amount of the spent catalyst.

26. The process according to claim 1 or 25, characterized in that 1-99% by weight of the total amount of the spent catalyst is not in the mixture of the coked catalyst and the spent catalyst regenerated in the regenerator.

27. The process according to claim 1, characterized in that the coke-burning regeneration is one-stage regeneration or two-stage regeneration, and said regenerated Y-zeolite containing catalyst is a partially regenerated or fully regenerated.

28. The process according to claim 1, characterized in that step (1) and step (2) are carried out in two catalyst-movable reactors respectively, the catalyst-movable reactors are selected from the group consisting of a fluidized bed, a riser, a descending transfer line reactor, a moving bed, a composite reactor of riser and fluidized bed, a composite reactor of riser and descending transfer line, a composite reactor of two or more risers, a composite reactor of two or more fluidized beds, a composite reactor of two or more descending transfer lines, and a composite reactor of two or more moving beds, wherein each of the reactors in the group comprises one or more reaction zones.

29. The process according to claim 1, characterized in that step (1) is carried out in a fluidized bed, and step (2) is carried out in a riser.

30. The process according to claim 28 or 29, characterized in that said riser is chosen from an iso-diameter riser, an equal-velocity riser, and various variable-diameter riser; and
said fluidized bed is chosen from a fixed fluidized bed, a particulate fluidization bed, a bubbling bed, a turbulent bed, a quick bed, a transfer bed, and a dense-phase fluidized bed.

31. The process according to claim 1, characterized in that the cooling of the first portion of the regenerated Y-zeolite containing catalyst is carried out in a direct heat exchange mode or an indirect heat exchange mode, wherein the catalyst is cooled to a temperature of 50-650° C.

32. The process according to claim 31, characterized in that said direct heat exchange mode is to carry out heat exchange by directly contacting the regenerated Y-zeolite containing catalyst with an air stream having a relatively low temperature, and the direct heat exchanger is in a fluidized bed or a riser; and the indirect heat exchange mode is to use an indirect heat exchanger, wherein the regenerated Y-zeolite containing catalyst passes through the tube side and steam passes through the shell side.

33. The process according to claim 1, characterized in that the weight ratio of the coked catalyst and the spent catalyst in the mixture regenerated in the regenerator is less than or equal to 1.0.

34. The process according to claim 1, characterized in that the organic oxygenate feedstock consists essentially of ethanol.

35. The process according to claim 1, characterized in that the organic oxygenate feedstock contains 1-100% of ethanol by the weight of organic oxygenate feedstock.

* * * * *